US011234705B2

(12) United States Patent
Li et al.

(10) Patent No.: US 11,234,705 B2
(45) Date of Patent: Feb. 1, 2022

(54) IMPLANT

(71) Applicant: Lifetech Scientific (Shenzhen) Co., Ltd., Shenzhen (CN)

(72) Inventors: Siyi Li, Shenzhen (CN); Liu Yang, Shenzhen (CN); Anning Li, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 323 days.

(21) Appl. No.: 16/464,601

(22) PCT Filed: Aug. 25, 2017

(86) PCT No.: PCT/CN2017/099028
§ 371 (c)(1),
(2) Date: May 28, 2019

(87) PCT Pub. No.: WO2018/107801
PCT Pub. Date: Jun. 21, 2018

(65) Prior Publication Data
US 2021/0093324 A1  Apr. 1, 2021

(30) Foreign Application Priority Data
Dec. 16, 2016  (CN) .......................... 201611170082.X

(51) Int. Cl.
*A61B 17/12* (2006.01)
(52) U.S. Cl.
CPC .. *A61B 17/12104* (2013.01); *A61B 17/12145* (2013.01); *A61B 2017/12054* (2013.01)

(58) Field of Classification Search
CPC .......... A61B 17/12145; A61B 17/1215; A61B 17/12104; A61B 2017/00862;
(Continued)

(56) References Cited

U.S. PATENT DOCUMENTS 5,185,908 A      2/1993  Oetiker
6,849,081 B2 *   2/2005  Sepetka ........... A61B 17/12022
                                                      606/1

(Continued)

OTHER PUBLICATIONS

International Search Report dated Nov. 20, 2017 for corresponding PCT Application No. PCT/CN2016/099028.

*Primary Examiner* — Julian W Woo
(74) *Attorney, Agent, or Firm* — Raymond Sun

(57) ABSTRACT

An implant (500) comprises an elastic deformation portion (51) and a connection portion (52) connected with the proximal end (511) of the elastic deformation portion (51), wherein the elastic deformation portion (51) is covered by an elastic outer layer (55); the proximal end of the connection portion (52) is surrounded by a tightening ring (58); and the proximal end of the elastic outer layer (55) is covered by the tightening ring (58). Since the proximal end of the elastic outer layer (55) of the implant (500) is surrounded by a tightening ring (58), the elastic outer layer (55) is closely attached on the connecting portion (52) of the implant (500), such that the elastic outer layer (55) can be prevented from being rolled over from the surface of the implant (500) when the implant (500) is implanted, thereby improving safety of lung volume reduction surgery.

18 Claims, 16 Drawing Sheets

(58) Field of Classification Search
CPC ... A61B 2017/00867; A61B 2017/1205; A61F 2/04; A61F 2002/043
See application file for complete search history.

(56) References Cited

U.S. PATENT DOCUMENTS

| | | | |
|---|---|---|---|
| 8,328,860 B2* | 12/2012 | Strauss | A61B 17/1219 623/1.11 |
| 9,636,116 B2* | 5/2017 | Rudakov | A61B 17/1204 |
| 9,848,882 B2* | 12/2017 | Lippert | A61B 17/12113 |
| 9,993,252 B2* | 6/2018 | Keeley | A61B 17/12022 |
| 11,110,248 B2* | 9/2021 | Pederson, Jr. | A61B 17/1214 |
| 2003/0065378 A1 | 4/2003 | Chevillon | |
| 2007/0239191 A1* | 10/2007 | Ramzipoor | A61B 17/12145 606/191 |
| 2015/0057700 A1* | 2/2015 | Chen | A61B 17/1214 606/200 |

* cited by examiner

IMPLANT

TECHNICAL FIELD

The present disclosure belongs to the technical field of interventional therapies, and relates to an implant for interventional therapy.

BACKGROUND ART

Percutaneous interventional techniques of implants for treating pulmonary emphysema have been reported in the literatures. That is, an elastic implant is delivered into a lung through a working channel of a bronchoscope in a form of a straight piece under the restriction of a delivery system. After the implant is delivered into a bronchus of a pulmonary emphysema area, the restriction of the delivery system on the implant is withdrawn, and the implant recovers and deforms to a natural shape (namely a shape in the absence of an external force). In the mean time, the pulmonary emphysema area is squeezed under the pulling action of the implant, and gas in the bronchus is exhausted, and the volume of a lung tissue in the pulmonary emphysema area is reduced, thereby allowing relatively healthy peripheral lung tissues to better exert its physiological functions.

The implant includes a metal substrate, and an elastic outer layer which is made of a macromolecular material and arranged on the surface of the metal substrate covering the metal substrate. When the implant is pushed into the bronchus of the pulmonary emphysema area through a delivery system, or when the implant is withdrawn back into the delivery system because of a poor half-release position, a limited binding force between the metal substrate and the elastic outer layer of the implant may possibly cause the elastic outer layer at the proximal end of the implant to separate from the metal substrate, which might damage the implant. A slotted hole is formed in the metal substrate, which allows the elastic outer layer to be embedded into the slotted hole of the metal substrate. Although this may increase the binding force between the metal substrate and the elastic outer layer, but because the wall of the metal substrate is relatively thin, so the opening of the slotted hole is formed to be relatively shallow, which limits the increase of the binding force between the elastic outer layer and the metal substrate. In addition, the hole may not be formed when a relatively small-sized implant is used, and the formation of the hole in the metal substrate may affect the rigidity of the metal substrate, and affect the overall safety of the implant.

SUMMARY OF THE INVENTION

The present disclosure is directed to solving the technical problem of providing an implant having an improved connection with an elastic outer layer. When the implant is implanted into a human body, it would be more difficult to separate the elastic outer layer from the implant, and thus the implant is safer and more reliable.

The present disclosure provides a technical solution below to solve the technical problem:

An implant includes an elastic deformation portion and a connection portion connected with a proximal end of the elastic deformation portion. The elastic deformation portion is covered by an elastic outer layer. A proximal end of the connection portion is provided with a tightening ring that forms an outer jacket surrounding the proximal end. A proximal end of the elastic outer layer is covered by the tightening ring.

In one embodiment of the technical solution, a first end of the tightening ring is provided with a connection plug, and a second end opposite to the first end is provided with an insertion slot corresponding with the connection plug, and used for inserting the connection plug.

In one embodiment of the technical solution, the tightening ring is provided with a thin slot connected with the insertion slot, and the thin slot is located on one side of the insertion slot away from the connection plug.

In one embodiment of the technical solution, the tightening ring is further provided with a through hole communicating with the insertion slot, and the through hole and the insertion slot are respectively located at two opposite ends of the thin slot.

In one embodiment of the technical solution, the connection plug has a T-shaped configuration, and the plug includes a head portion and a neck portion connected with the head portion. The axial width of the neck portion is less than that of a connection part which connects the head portion with the neck portion.

In one embodiment of the technical solution, the axial width of the head portion of the connection plug is gradually increased along a direction close to the neck portion.

In one embodiment of the technical solution, an included angle of the inner edge of the head portion of the connection plug along the axial line of the tightening ring is 45 to 85 degrees.

In one embodiment of the technical solution, the center of the through hole is located on an extension line of the center line of the thin slot of the tightening ring.

In one embodiment of the technical solution, the ratio of the diameter of the through hole to the width of the tightening ring ranges between 0.2:1 and 0.6:1.

In one embodiment of the technical solution, the implant is a lung volume reduction implant.

In one embodiment of the technical solution, the elastic deformation portion has a shape memory characteristic, and under the application of the same external force, a flexible guide portion deforms more easily than the elastic deformation portion. The proximal end of a connection member is further provided with a boss. The outer diameter of the boss is greater than that of a portion of the elastic implant that is close to the boss when in a delivery state.

In one embodiment of the technical solution, under the application of the same external force, the flexible guide portion deforms more, and more easily, from the proximal end to the distal end.

In one embodiment of the technical solution, under the application of the same external force, the connection portion deforms more easily than the elastic deformation portion.

In one embodiment of the technical solution, the connection portion is provided with a plurality of cutting slots in a spaced-apart manner along a lengthwise direction of the connection portion, and all the cutting slots of the connection portion are communicated with a lumen of the connection portion.

In one embodiment of the technical solution, the connection portion includes multiple hollow sub-components connected end to end. The proximal end of each hollow sub-component includes multiple proximal end protrusions distributed along a circumferential direction of the hollow sub-component. The circumferential length of each proximal end protrusion from the proximal end to the distal end is gradually decreased, and a proximal end groove is formed between two adjacent proximal end protrusions. The distal end of each hollow sub-component includes multiple distal end protrusions distributed along the circumferential direction of the hollow sub-component. The circumferential length of each distal end protrusion from the proximal end to the distal end is gradually increased, and a distal end groove is formed between two adjacent distal end protrusions.

In one embodiment of the technical solution, part of the distal-end face of the boss is sunken towards the proximal end of the boss to form an annular groove surrounding the longitudinal center axis of the boss.

In one embodiment of the technical solution, part of the side surface of the boss is sunken into the inside of the boss to form an annular groove surrounding the longitudinal center line of the boss.

In one embodiment of the technical solution, the boss includes multiple small protrusions distributed in a spaced-apart manner along the circumferential direction of the boss.

According to the implant of the present disclosure, the proximal end of the connection portion is provided with the tightening ring that forms an outer jacket surrounding the proximal end, and the tightening ring may provide a relatively uniform compression force from the circumferential direction to the macromolecular elastic outer layer at the proximal end of the connection portion, so the elastic outer layer is fixed to the outer surface of the connection portion more closely and firmly, so as to prevent the elastic outer layer from rolling over, and also improving the safety of lung volume reduction surgery.

During installation of the tightening ring on the implant of the present disclosure, only the connection plug is required to be aligned with the insertion slot, and an external force is applied to insert the connection plug into the insertion slot, and after the external force is withdrawn, the connection plug may be clamped in the insertion slot, so that the operation is more convenient. The implant is of a relatively small size, so that it is convenient to set the tightening ring, and the installation process of the tightening ring may be greatly simplified.

BRIEF DESCRIPTION OF THE DRAWINGS

The present disclosure will be further described below in combination of accompanying drawings and embodiments. In the drawings.

DETAILED DESCRIPTION OF THE INVENTION

To make the above-mentioned objectives, features and advantages of the present disclosure more obvious and understandable, specific embodiments of the present disclosure are described in detail below in combination with the accompanying drawings. Many specific details are described in the following descriptions so as to fully understand the present disclosure. However, the present disclosure may be implemented in many other ways different from those described herein. Any person skilled in the art can make similar improvements without departing from the intension of the present disclosure, so that the present disclosure will not be limited by the following disclosed specific embodiments.

In the interventional field, generally, the end relatively close to an operator is defined as a proximal end, and the end relatively far from the operator is defined as a distal end.

Unless otherwise defined, all technical and scientific terms used herein are the same as the meanings according to the general understandings of those skilled in the art of the present disclosure. The terms used in the description of the present disclosure in this text are merely to describe the specific embodiments, but not intended to limit the present disclosure. The terms "and/or" used herein include any and all combinations of one or more related listed items.

The spirit of the present invention is to arrange a tightening ring at the proximal end of a connection portion of an implant having a surface covered by a macromolecular material layer to prevent an elastic outer layer on the connection portion from rolling up or being damaged, so as to guarantee the structural integrity of the elastic implant. The implant is not limited to a lung volume reduction elastic implant, but may also be other interventional medical devices having a surface covered by the macromolecular material layer. The shape and the structure of the tightening ring are not limited to the descriptions of the following embodiments as long as the head and tail ends are connected with each other to form a ring-like object. For example, the tightening ring may be a ring-like object directly formed by connecting the head and tail ends in a clamping or welding manner. Further, the shapes and the structures of a connection plug and an insertion slot of the tightening ring are not limited to the descriptions of the following embodiments either, as long as the connection plug may be clamped in the insertion slot to form the annular tightening ring, or the connection plug may be welded with the insertion slot to form the tightening ring, or the connection plug is clamped in the insertion slot and the connection plug and the insertion slot are welded to form the annular tightening ring. The implant of the present disclosure is described by taking a lung volume reduction elastic implant as an example.

Figure 1:
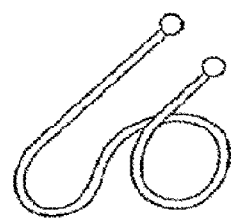
FIG. 1 is a structural schematic diagram of an elastic implant in the prior art.
Figure 2:
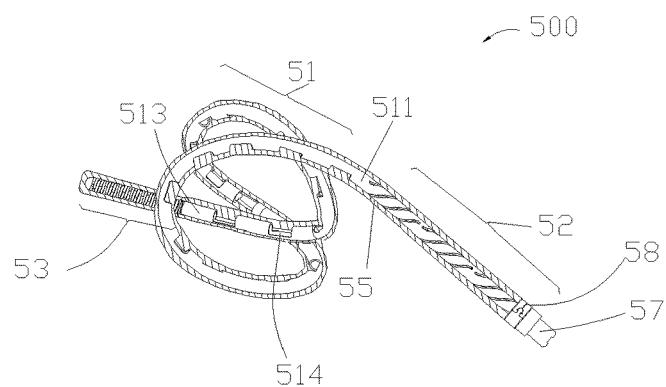
FIG. 2 is a schematic diagram of an implant provided by one embodiment of the present disclosure after part of a thin film of the implant is torn off.
Figure 4:
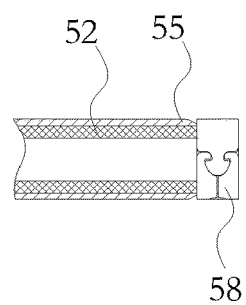
FIG. 4 is a partial sectional view of a connection portion of the implant shown in FIG. 3.

Referring to FIG. 2 and FIG. 4 together, an implant 500 provided by one embodiment of the present disclosure is of a tubular structure, and includes an elastic deformation portion 51, a flexible guide portion 53 connected with the distal end of the elastic deformation portion 51, a connection portion 52 connected with the proximal end of the elastic deformation portion 51, a connection member 57 connected with the proximal end of the connection portion 52, and an elastic outer layer 55. A portion of the proximal end of the connection portion 52 adjacent to the connection member 57 is provided with a tightening ring 58 that forms an outer jacket surrounding the proximal end of the connection portion. The elastic outer layer 55 covers the outer wall of the implant 500. Specifically, the proximal end of the elastic outer layer 55 is flush with the proximal end of the connection portion 52 and is covered by the tightening ring 58. The distal end portion of the elastic outer layer 55 is flush with the distal end portion of the implant 500 so as to cover the outer wall of the implant 500. It can be understood that the proximal end portion of the elastic outer layer 55 is flush with the proximal-end face of the tightening ring 58. The elastic deformation portion 51 and the flexible guide portion 53 may be made in one piece, or also may be fixedly connected. The distal end of the flexible guide portion 53 is the distal end of the elastic implant 500. Under the application of the same external force, the flexible guide portion 53 deforms more easily than the elastic deformation portion 51 (that is, under the application of the same external force, the anti-bending performance of the flexible guide portion 53 is lower than that of the elastic deformation portion 51), so that the flexible guide portion 53 can move more effectively in a bronchus without injuring surrounding tissues. The elastic outer layer 55 may reduce bronchitis and injury to the bronchus due to friction of the implant and the inner wall of the bronchus in a respiratory process to lower the risk of pneumonia and infections of the small airway, and may effectively reduce the release of metal elements. In addition, as it is arranged at the proximal end of the connection portion 52 in a covering manner, the tightening ring 58 may provide a circumferentially relatively uniform compression force to compress the elastic outer layer 55 covering the outer surface of the implant 500 after the head and tail ends of the tightening ring 58 are connected to form a ring-like object, so as to allow the elastic outer layer 55 to cover the outer surface of the connection portion 52 more closely and firmly, which increases a binding force between the elastic outer layer 55 and a metal substrate of the connection portion 52, thereby preventing the elastic outer layer 55 from being separated from the implant 500, and avoiding damage to the integrity of the implant, and thereby improving the safety of lung volume reduction surgery.

Figure 3:
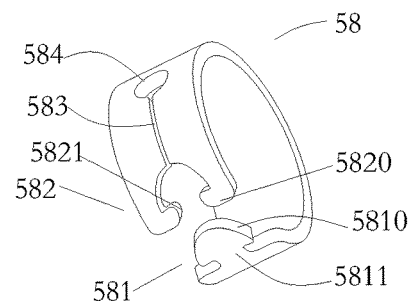
FIG. 3 is a structural schematic diagram of a tightening ring of the implant shown in FIG. 2.

As shown in FIG. 2, in the present disclosure, the head and tail ends of the tightening ring 58 are connected to form a circular ring shape. Referring to FIG. 2 and FIG. 3 together, the tightening ring 58 may be formed by bending a rectangular sheet, and has a certain elasticity. The head end of the rectangular sheet is a first end of the tightening ring 58, and the tail end of the rectangular sheet is a second end of the tightening ring 58. After the rectangular sheet is bent into a ring shape, its head end faces its tail end, namely the first end faces the second end. The first end is provided with a connection plug 581 which may be directly cut from the first end of the tightening ring 58. It can be understood that the connection plug 581 also may be connected with a main body of the tightening ring 58 by welding, or may be connected in other ways, and there is no limitation here as to the manner of connection. In the present embodiment, the specific shape of the connection plug 581 approximates a dumbbell shape. The overall T-shaped connection plug 581 includes a head portion 5810 and a neck portion 5811 connected with the head portion 5810. The neck portion 5811 connects the head portion 5810 of the tightening ring 58 with the main body section. The axial width of the neck portion 5811 of the connection plug 581 is less than that of a portion which is located at a connection portion of the head portion 5810 of the connection plug and the neck portion 5811, and the axial direction here is along an axial direction of the tightening ring. It can be understood that the outer surface of the head portion 5810 in the present embodiment is an arcuate surface, and the outer surface of the head portion 5810 in other embodiments also may be planar. The width of the head portion 5810 gradually increases as it gets closer to the neck portion 5811. The axial width of the neck portion 5811 is less than that of the portion which is located at a connection portion of the head portion 5810 and the neck portion 5811, so a clamping slot-shaped recess may be formed in the position of a joint of the head portion 5810 and the neck portion 5811, and the direction of the recess is towards the axial line of the neck portion 5811. The outer surface that is opposite to the insertion slot of the head portion of the connection plug 581 is designed as a smooth arcuate surface to ensure that it is easier to provide a first protruding edge 5820 and a second protruding edge 5821 which are opposite to each other in a slotted hole of the insertion slot 582 when the connection plug 581 is inserted into the insertion slot 582, so as to allow the connection plug 581 to be inserted more smoothly into the insertion slot 582. As the axial width of the connection plug 581 in the direction close to the neck portion 5811 is gradually increased, it can be understood that the entire head portion 5810 of the connection plug 581 approximates the shape of an arrow. The connection plug may also be of other shapes, such as a cone or a column, and there is no specific limitation here.

Figure 5:
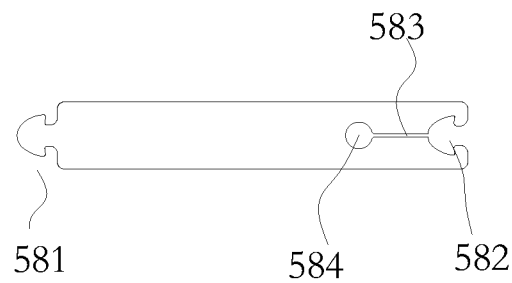
FIG. 5 is a structural schematic diagram of the tightening ring of FIG. 3 shown in a spread-out configuration.

Referring to FIG. 3 and FIG. 5 together, the second end of the tightening ring 58 is provided with the insertion slot 582 having a U-shaped open structure. The first protruding edge 5820 and the second protruding edge 5821, which are opposite to each other, are respectively arranged at the opening. A space for insertion is formed between the first protruding edge 5820 and the second protruding edge 5821. The first protruding edge 5820 and the second protruding edge 5821 have the same shape and are opposite to each other. Each protruding edge is of an L shape on a whole. The portions of the inner surfaces of the first protruding edge and the second protruding edge that are close to the innermost side of the insertion slot 582 are both arcuate surfaces, and their radians correspond to the radian of the outer surface of the head portion of the connection plug 581. When the connection plug 581 is inserted into the insertion slot 582, the outer surface of the head portion of the connection plug 581 may be completely fitted to the inner surfaces of the first protruding edge 5820 and the second protruding edge 5821, and the space encircled by the first protruding edge 5820 and the second protruding edge 5821 is filled with the connection plug 581. Furthermore, the inner and outer surfaces of the connection plug 581 will not protrude from the inner and outer surfaces of the first protruding edge 5820 and the inner and outer surfaces of the second protruding edge 5821, thereby ensuring that after the tightening ring 58 is tightened, the surfaces of the inserted portions are in snug fit, and the starting part of the elastic outer layer covered below will not be exposed.

Figure 10:
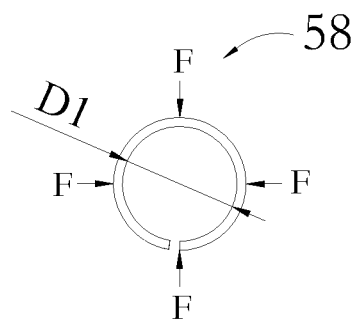
FIG. 10 is a side view of the tightening ring of FIG. 3 shown in a non-tightened state.
Figure 11:
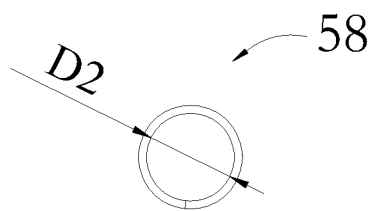
FIG. 11 is a side view of the tightening ring of FIG. 3 shown in a tightened state.

Referring to FIG. 2, FIG. 7, FIG. 8 and FIG. 9 together, the tightening ring 58 is provided with a thin slot 583 that communicates with the insertion slot 582 and is located on a side of the insertion slot 582 away from the connection plug 581. The tightening ring 58 is further provided with a through hole 584 which communicates with the insertion slot 582 through the thin slot 583. The through hole 584 and the insertion slot 582 are respectively located at two opposite ends of the thin slot 583. During tightening of the tightening ring 58, when a radial force F is applied to the tightening ring 58, the first end and the second end of the tightening ring 58 move closer to each other, and the connection plug 581 contacts the first protruding edge 5820 and the second protruding edge 5821 of the insertion slot 582. When the connection plug 581 contacts the first protruding edge 5820 and the second protruding edge 5821 of the insertion slot 582, the radial force F is continuously applied, and the first protruding edge 5820 and the second protruding edge 5821 separate from each other under the pushing of the connection plug 581, that is, the opening of the insertion slot 582 is enlarged. When the first protruding edge 5820 and the second protruding edge 5821 contact the connection plug 581, the insertion slot 571 may experience elastic deformation, and the thin slot 583 may experience the elastic deformation to become a trapezoidal slot from a rectangular slot, and the opening of a portion that is close to the insertion slot 582 of the thin slot 583 is enlarged. The arrangement of the through hole 584 and the thin slot 583 disperses the stress in this area to prevent plastic deformation of the insertion slot 582, so as to ensure that an elastic force for shape recovery may be generated after the opening of the insertion slot 582 is enlarged. The provision of the through hole 584 may ensure that the slot opening of the insertion slot 582 may still recover its initial shape after being expanded. After the opening of the insertion slot 582 is enlarged, the connection plug 581 may be inserted into the insertion slot 582, and the first protruding edge 5820 and the second protruding edge 5821 of the insertion slot 582 are reset to their initial positions under the application of the elastic force. The first protruding edge 5820 and the second protruding edge 5821 may simply contact the neck portion 5811 of the connection plug 581 so as to be hooked with the head portion 5810 of the connection plug 581 to ensure that the connection plug 581 will not disengage from the insertion slot 582, and thus the tightening of the implant is completed. Referring to FIG. 10 and FIG. 11 together, before the tightening ring is tightened, its diameter D1 is slightly greater than the outer diameter of the connection portion of the implant to ensure that the tightening ring may be arranged on the implant in a covering manner. The circumferential force F is applied to the tightening ring to insert the connection plug into the insertion slot. After the connection plug is inserted into the insertion slot, the diameter of the tightening ring is decreased to D2, and thus the tightening of the implant is completed. The range of D1 to D2 varies between 1 percent and 5 percent, and an operator can determine the specific variation depending on the clinical situation. This tightening mode may provide a circumferentially relative uniform compression to compress the elastic outer layer of the implant to allow the elastic outer layer to be fixed on the outer surface of the connection portion more closely and firmly, which increases the binding force between the elastic outer force and the connection portion. During implantation of the implant, under the tightening action of the tightening ring, the connection between the elastic outer layer and the connection portion is closer and firmer, so the operation in the implantation of the implant is safer.

Further, referring to FIG. 3, in the present embodiment, the distance between the first protruding edge 5820 and the second protruding edge 5821 is greater than or equal to the axial width of the neck portion 5811 of the connection plug 581. The distance between the first protruding edge 5820 and the second protruding edge 5821 herein refers to a distance between the first protruding edge 5820 and the second protruding edge 5821 in its natural state. The distance between the first protruding edge 5820 and the second protruding edge 5821 is greater than or equal to the axial width of the neck portion 5811 of the connection plug 581 to ensure that after the connection plug 581 is inserted into the insertion slot 582, the first protruding edge 5820 and the second protruding edge 5821 may contact the two sides of the neck portion 5811 of the connection plug 581. If the distance between the first protruding edge 5820 and the second protruding edge 5821 is too short, the first protruding edge 5820 and the second protruding edge 5821 are still in a stressed state after the connection plug is inserted into the insertion slot, and extend beyond the axial line of the tightening ring 58, which gives rise to protruding corners on the outer circumference of the tightening ring 58 and thus affects the implantation of the implant.

Figure 6:
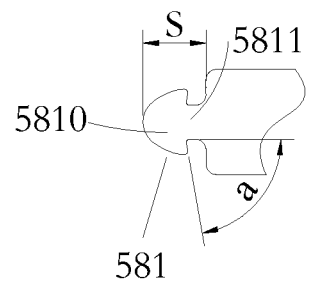
FIG. 6 is a partial structural schematic diagram of the tightening ring shown in FIG. 3.
Figure 7:
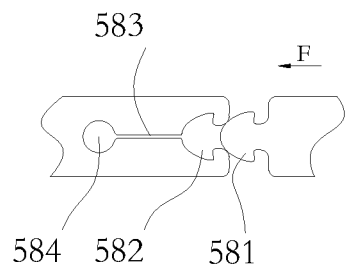
FIG. 7 is a schematic diagram of a tightening process of the tightening ring shown in FIG. 3.
Figure 8:
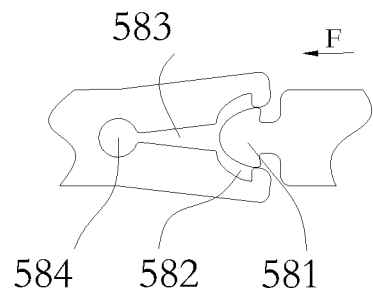
FIG. 8 is a schematic diagram of a tightening process of the tightening ring shown in FIG. 3.
Figure 9:
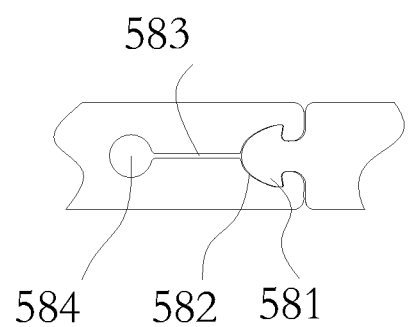
FIG. 9 is a schematic diagram of a tightening process of the tightening ring shown in FIG. 3.

Further, referring to FIG. 6, after the tightening ring spreads into a straight line, an included angle a between the inner edge of the head portion of the connection plug 581 and the axial line of the tightening ring is 45 to 85 degrees to ensure that the connection plug 581 will not disengage after being inserted into the insertion slot. If the included angle a is more than 85 degrees, the degree to which the protruding edges of the insertion slot and the connection plug 581 mesh is relatively low after the connection plug 581 is inserted into the insertion slot; and under the application of the elastic force, the connection plug 581 can be easily separated from the protruding edges of the insertion slot, which may result in the connection plug 581 disengaging from the insertion slot. When the included angle a is less than 45 degrees, the length of the connection plug 581 is increased under the same axial width, which gives rise to an extremely large feed amount of the tightening ring during tightening, and thus leads to an extremely small diameter of the tightening ring after the connection plug 581 is inserted into the insertion slot, and the extremely small diameter may generate a relatively high compression pressure acting on the elastic outer layer covered by the tightening ring, and thereby damaging the elastic outer layer. Therefore, the included angle a here is preferably 45 to 85 degrees, which would guarantee the tightening stability of the tightening ring and also guarantee no damage to the elastic outer layer of the implant.

Further, as shown in FIG. 5, in the present embodiment, the center of the through hole 584 is located on an extension line of the center line of the thin slot of the tightening ring. The main objective of arranging the center of the through hole 584 on the horizontal axial line of the tightening ring is to maintain the second end of the entire tightening ring in axial symmetry, so that after the connection plug 581 is inserted into the insertion slot 582, the first protruding edge and the second protruding edge experience relatively uniform stress, and have approximately the same elastic deformations. Meanwhile, the through hole may disperse the stress of this area more effectively to prolong the service life of the tightening ring. The ratio of the diameter of the through hole to the width of the tightening ring is between 0.2:1 and 0.6:1. If the diameter of the through hole is too large, this would affect the strength of the whole tightening ring. If the diameter of the through hole is too small, the stress dispersion effect of the through hole is relatively poor, and thus the insertion slot 582 produces plastic deformation easily. As a result, the springback effect is lowered after the slot opening is expanded, and it is difficult to separate the first protruding edge and the second protruding edge of the tightening ring, which affects the simplicity and the convenience of the operation of the tightening ring. The ratio of the diameter of the through hole to the width of the tightening ring is set between 0.2:1 and 0.6:1 to guarantee a relatively good stress dispersion effect, and to improve the hardness of the tightening ring to the maximum extent.

In the embodiment of the present disclosure, the through hole 584 is a circular hole. In other embodiments, the through hole 584 may also be a square hole, an elliptical hole or holes of other shapes.

In other embodiments of the present disclosure, the thin slot 583 and the through hole 584 may be both omitted, or the through hole 584 may be omitted, and the connection plug 581 is directly pressed into the insertion slot 582. To enhance the binding of the connection plug 581 and the insertion slot 582, they are directly welded.

Figure 12:
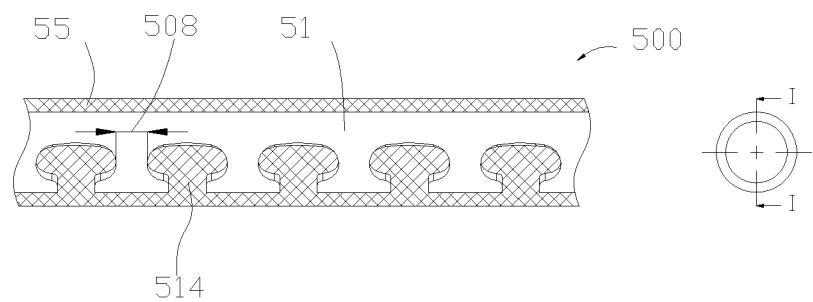
FIG. 12 is a partial sectional view of the implant in FIG. 2.
Figure 13:
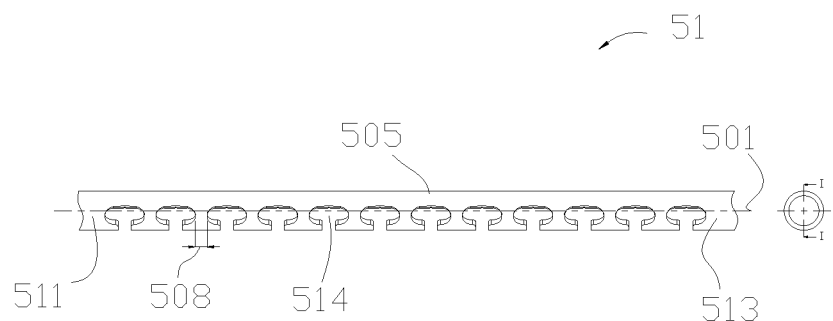
FIG. 13 is a sectional view of an elastic deformation portion of the implant shown in FIG. 2.

Referring to FIG. 2, FIG. 12 and FIG. 13, the elastic deformation portion 51 has a shape memory characteristic, and includes a proximal end 511 and a distal end 513 which are opposite to each other. The distal end 513 is connected with the flexible guide portion 53. The elastic deformation portion 51 further includes multiple mutually isolated cutting slots 514 communicating with the lumen of the elastic deformation portion 51. The multiple cutting slots 514 allow the elastic deformation portion 51 of the elastic implant 500 to bend into a predetermined shape in the natural state, such as a shape as shown in FIG. 2.

The elastic deformation portion 51 has a predetermined curled shape in the natural state (in the absence of external force), may be restrained into a straight piece shape or any other shapes under the action of an external force, and recovers to the predetermined shape through bending and torsion after the external force is withdrawn. The elastic deformation portion 51 may be made of a material commonly used in the industry and having a shape memory function. In the present disclosure, there is no limitation to specific materials as long as this material is applicable to the human body and has the shape memory function. In the present embodiment, the elastic deformation portion 51 is made of a nickel-titanium alloy and has a diameter of about 0.5-2.0 mm and a wall thickness of 0.01-0.4 mm.

Figure 14:
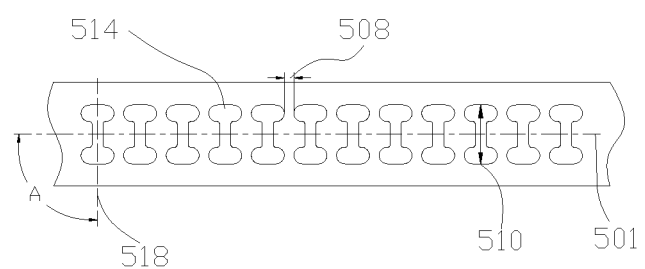
FIG. 14 is a schematic diagram of cutting slots of the elastic deformation portion of the implant in FIG. 2 after the elastic deformation portion is cut away along its lengthwise direction and unfolded.

Referring to FIG. 13 and FIG. 14 together, in the present embodiment, to allow the elastic deformation portion 51 to extend into a thinner bronchus and achieve a better compression effect on corresponding tissues, preferably, a conical nickel-titanium tube having a consistent inner diameter and a gradually varying wall thickness is adopted, such as a conical nickel-titanium tube having an inner diameter of 0.8-1.0 mm and a wall thickness varying from 0.01 mm at the distal end to 0.4 mm at the proximal end. Multiple dumbbell-shaped cutting slots 514 are formed in the nickel-titanium tube. The extension direction (namely the incision direction) 518 of these cutting slots 514 and the axial line 501 of the elastic deformation portion 51 form a certain angle A. Preferably, the angle A is 10-90 degrees. A gap 508 of about 0.05-0.5 mm is provided between two adjacent cutting slots 514. It can be understood that as the elastic deformation portion 51 has the multiple cutting slots 514, the anti-bending performance of the elastic deformation portion 51 may vary with changes of the lengths 510 of the cutting slots 514 in the extension direction 518. Those skilled in the art can set the lengths 510 of the cutting slots 514 of the elastic deformation portion 51 in the extension direction 518 based on clinical requirements so to make the anti-bending performance of the flexible guide portion 53 lower than that of the elastic deformation portion 51.

Figure 15:
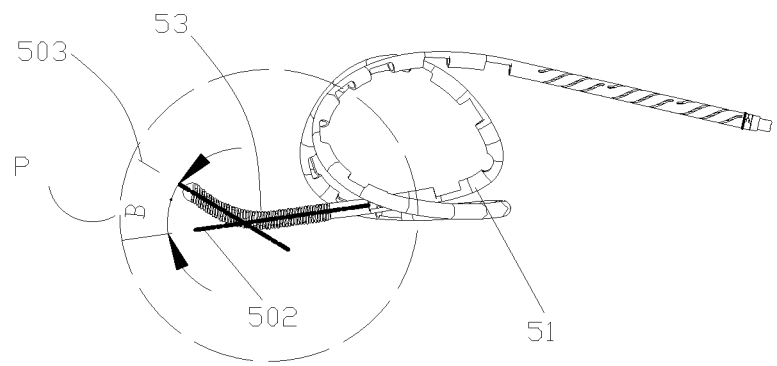
FIG. 15 is a schematic diagram of the implant in FIG. 2 shown without a thin film.
Figure 16:
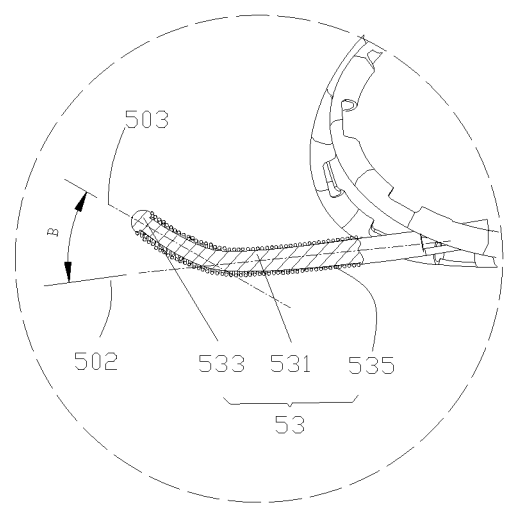
FIG. 16 is an enlarged view of the area P in FIG. 15.

Referring to FIG. 15 and FIG. 16 together, the flexible guide portion 53 is located at the distal end of the elastic deformation portion 51 and used for guiding the elastic deformation portion 51, and deforms more, and more easily, from the proximal end to the distal end under the application of the same external force. The axial line 503 of the distal end of the flexible guide portion 53 and the axial line 502 of the distal end 511 of the elastic deformation portion 51 form an included angle B of 5-60 degrees. In the present embodiment, the flexible guide portion 53 includes a main body section 531, a flexible guide portion head end 533 arranged at the distal end of the main body section 531 and a spring 535 arranged on the outer wall of the main body section 531.

The main body section 531 supports the spring 535 and may be made of a relatively high elasticity metal such as a nickel-titanium alloy or a cobalt-chromium alloy, and the outer diameter of the main body section 531 is gradually increased from the distal end of the main body section 531 to the proximal end of the main body section 531. The proximal end of the main body section 531 is connected with the distal end 511 of the elastic deformation portion 51 using techniques of covering a macromolecular thermal shrinkage tube or thin film, gluing, laser welding, soldering, and the like. In the present embodiment, the main body section 531 is a solid nickel-titanium rod. It can be understood that the main body section 531 also may be a hollow nickel-titanium tube. When the main body section 531 is a hollow nickel-titanium tube, the outer diameter of the main body section 531 is gradually increased from the distal end to the proximal end if the inner diameter of the main body section 531 is unchanged from the proximal end to the distal end, and the inner diameter of the main body section 531 is gradually decreased from the distal end to the proximal end if the outer diameter of the main body section 531 is unchanged from the proximal end to the distal end.

In the present embodiment, the distal end of the spring 535 and the distal end of the main body section 531 are fused together to form the flexible guide portion head end 533. The flexible guide portion head end 533 is coaxial with the distal end of the main body section 531 and closes the distal end of the main body section 531. The flexible guide portion head end 533 may be further provided with a developing mark (not shown in the figures).

The spring 535 is wound by a metal wire (preferably a tungsten metal wire, a tantalum metal wire and other metal wires having relatively high X-ray developing performance) having a wire diameter of 0.05-0.5 mm. It can be understood that the flexible guide portion head end 533, the spring 535 and the main body section 531 also may be molded respectively and are connected together by a conventional process. During separate molding, the flexible guide portion head end 533 is preferably made of a metal such as tungsten or tantalum having relatively high X-ray developing performance. It can be further understood that the flexible guide portion head end 533 may be omitted as required.

It can be further understood that when the flexible guide portion head end 533 is omitted and the main body section 531 is a hollow nickel-titanium tube, on one hand, a closing member made of the same or similar material as the guide head 533 may be arranged in the proximal end of the main body section 531 to fully or partially close the distal end of the elastic deformation portion 51; and on the other hand, the proximal end of the main body section 531 may also communicate with the elastic deformation portion 51, and at the moment, the proximal end and the distal end of the implant 500 are both opened. Any arrangement is possible as long as the core wire (specifically described below) does not pass through the distal end of the flexible guide portion 53. That is, when the distal end of the implant 500 is opened, the core wire enters the implant 500 and the outer diameter of the core wire is greater than the diameter of an inscribed circle of the opening in the distal end of the implant 500 (when the opening is a non-circular opening such as a triangular opening or a square opening) or the diameter of the opening in the distal end (when the opening is a circular opening).

Figure 17:
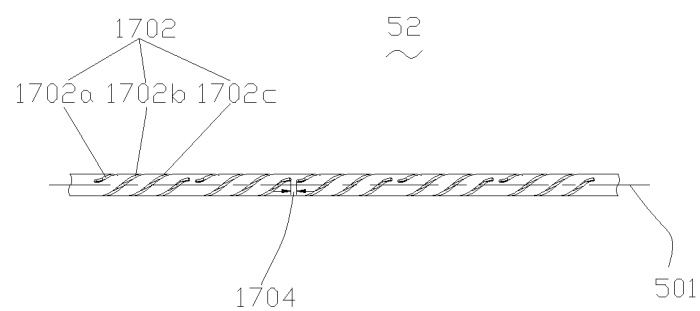
FIG. 17 is a schematic diagram of a connection portion of the implant in FIG. 2.
Figure 18:
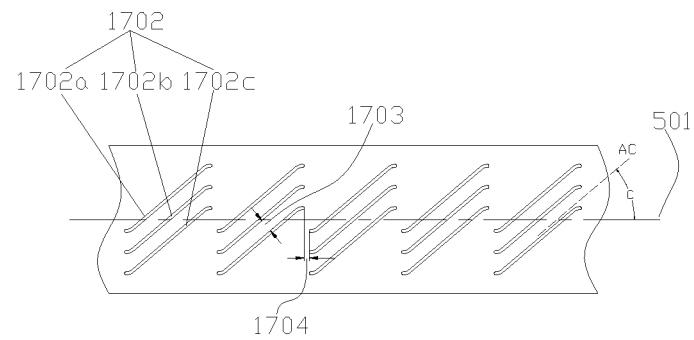
FIG. 18 is a schematic diagram of the connection portion of FIG. 17 after the connection portion is cut away along its lengthwise direction and unfolded.

Referring to FIGS. 2, 17 and 18 together, the connection portion 52 is connected between the connection member 57 and the elastic deformation portion 51. Under the application of the same external force, the anti-bending performance of the connection portion 52 is lower than that of the elastic deformation portion 51 (namely under the application of the same external force, the connection portion 52 deforms more easily than the elastic deformation portion 51). In the present embodiment, the connection portion 52 is provided with multiple cutting slot groups 1702. After the connection portion 52 is cut along the axial direction and spread out, it can be seen that each cutting slot group 1702 includes three cutting slots 1702a, 1702b and 1702c arrayed along the circumferential direction of the connection portion 52 and parallel to one another. Two ends of the three cutting slots are aligned with each other in the circumferential direction. A certain gap 1703 is provided between two adjacent cutting slots in each cutting slot group 1702, and a gap 1704 is provided between two adjacent cutting slot groups 1702. Each cutting slot has a slim profile, and the extension direction AC of the multiple cutting slots and the axial line 513 of the connection portion 52 form a certain included angle C. By adjusting the number of the cutting slots in each cutting slot group 1702, the size of each gap 1703, the size of the included angle C between the extending direction AC of the cutting slots and the axial line 501 of the elastic deformation portion 51 and the size of the gap 1704 between two adjacent cutting slot groups 1702, the anti-bending performance of the whole connection portion 52 may be adjusted to be lower than that of the elastic deformation portion 51. In other embodiments, each cutting slot group 1702 may include 2-6 culling slots, the gap 1703 between two adjacent cutting slots in each cutting slot group 1702 is 0.05-1 mm, the included angle C is 10-85 degrees, and the gap 1704 between two groups is 0.1-1.0 mm. The elastic deformation portion 51 has an outer diameter of about 1.0-2.0 mm and a wall thickness of 0.05-0.3 mm. The connection between the connection portion 52 and the elastic deformation portion 51 may be accomplished by techniques such as covering of a macromolecular thermal shrinkage tube or thin film, gluing, laser welding, soldering, and the like. On the basis of the prior art, integrated cutting is preferred, and the elastic deformation portion 51 and the connection portion 52, which have different textural features, are cut from different areas on the same tube.

Figure 19:
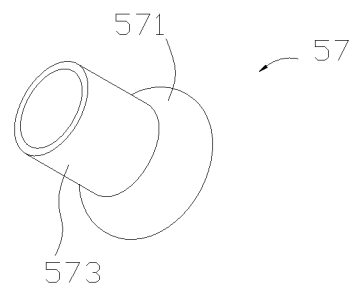
FIG. 19 is a schematic diagram of a connection member of the implant in FIG. 2.
Figure 20:
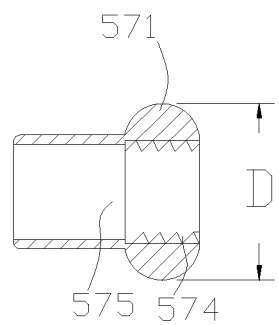
FIG. 20 is a sectional view of the connection member in FIG. 19.
Figure 21:
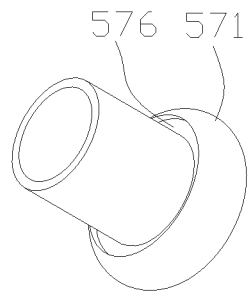
FIG. 21 is a schematic diagram of the deformation of the connection member in FIG. 19.
Figure 22:
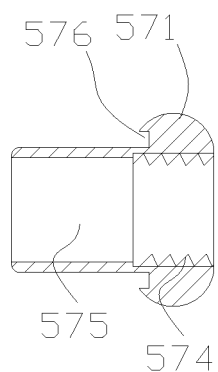
FIG. 22 is a sectional view of the connection member in FIG. 21.

Referring to FIG. 19 and FIG. 20 together, the connection member 57 is located at the proximal end of the connection portion 52 and includes a boss 571 and a connection section 573. The outer diameter D of the boss 571 is greater than the outer diameter of the portion close to the boss 571 of the elastic implant 500 when in a delivery state. In the present implementation mode, the outer diameter of the portion close to the boss 571 of the elastic implant 500 in the delivery state is the outer diameter of the proximal end of the connection portion 52. An internal thread 574 is arranged inside the boss 571. The connection section 573 is located between the boss 571 and the connection portion 52, and is provided with a cavity 575 extending through the proximal-end face and the distal-end face of the connection section 573. In the present embodiment, the cross section that is parallel to the longitudinal center axis of the boss 571 includes two opposite semicircles. The outer diameter D may not exceed 2.8 mm and is preferably 2.0-2.3 mm. The boss 571 effectively enlarges a contact area of the proximal end of the elastic implant 500 and the bronchus to reduce injury to the lung tissues after the elastic implant 500 is implanted. It can be understood that part of the distal-end face of the boss 571 may also be sunken towards the proximal end of the boss 571 to form an annular groove 576 (see FIGS. 21 and 22) surrounding the longitudinal center line of the boss 571 to provide a fastening position for a biopsy forceps, so that the biopsy forceps clamp a connection apparatus more effectively to withdraw the elastic implant 500.

Referring to FIG. 2 and FIG. 12 together, the elastic outer layer 55 completely covers the outer surface of the elastic implant 500 except the boss 571 and fills each cutting slot 514 without blocking the lumen of the elastic implant 500, thereby ensuring that the elastic outer layer 55 firmly covers the elastic implant 500 and guaranteeing no blockage in the lumen of the elastic implant 500. The elastic outer layer 55 may be 0.01-0.8 mm in thickness. The elastic outer layer 55 may be made of a macromolecular solution having the following features: good chemical stability, water resistant and weather resistant, good lower compressibility, good biocompatibility, high mechanical strength, nontoxicity, odorless, and the like. For example, these macromolecular solutions may be silicone rubber or polyurethane solutions. Because of the basic bonding characteristics of the elastic outer layer 55 and the metal substrate, it is easy for the proximal end portion of the elastic outer layer 55 to roll over or fall off under the application of an external force, and since the outer diameter of the boss 571 is greater than that of the portion close to the boss 571 of the elastic implant 500 in the delivery state, so the boss 571 can protect the proximal end portion of the elastic outer layer 55 from being in contact with a vascular wall during the delivery or withdrawal processes, and thereby protect the elastic outer layer 55 from rolling over or falling off during the delivery and withdrawal processes.

Figure 23:
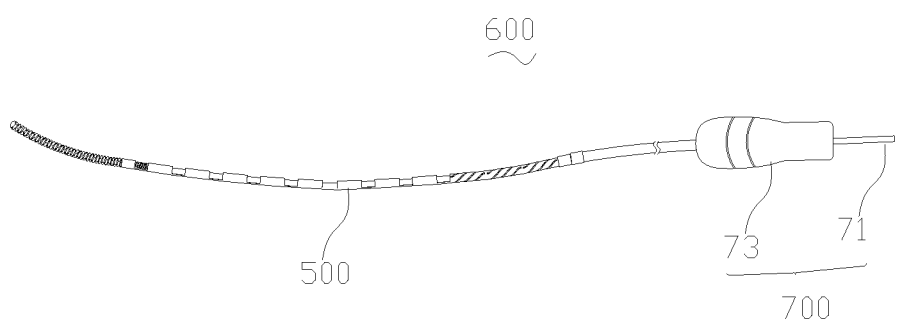
FIG. 23 is a schematic diagram of a lung volume reduction device provided by one embodiment of the present disclosure.
Figure 24:
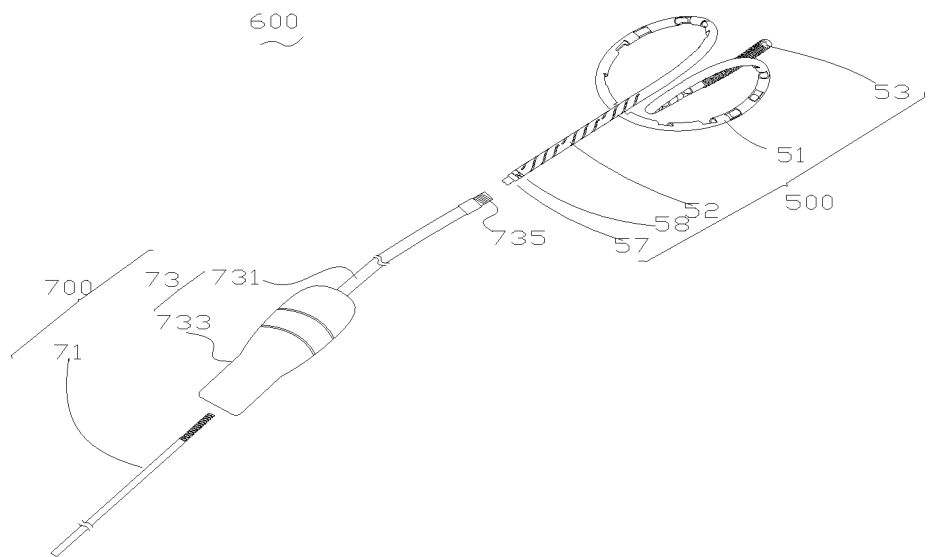
FIG. 24 is an exploded schematic diagram of the lung volume reduction device in FIG. 23.

Referring to FIGS. 23 and 24 together, a lung volume reduction device 600 provided by one embodiment of the present disclosure includes an elastic implant 500 and a delivery apparatus 700. The delivery apparatus 700 includes a core wire 71 and a pushing mechanism 73.

The core wire 71 is accommodated in the lumen of the elastic implant 500 to restrain the elastic implant 500 into an approximately linear delivery state to conveniently deliver the implant 500 to a lesion locus, so a delivery sheath for restraining the implant 500 is no longer needed, which avoids any injury caused by the delivery sheath to a trachea during the delivery process, and further reduces the incidence rate of pneumothorax. The core wire 71 may be made of a section of metal wire having a diameter of 0.1-1.1 mm. Compared with the prior art, the implant 500 does not need a delivery sheath, and may be implanted into a lung bypass or the tail ends of certain tracheas having small diameters to achieve a better therapeutic effect.

Figure 25:
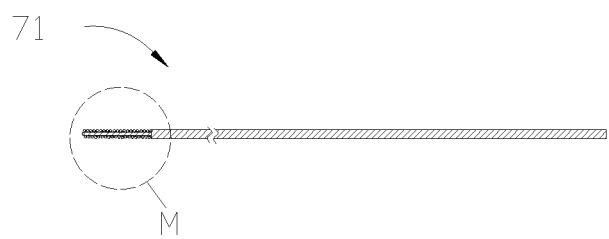
FIG. 25 is a schematic diagram of a core wire of the lung volume reduction device in FIG. 23.
Figure 26:
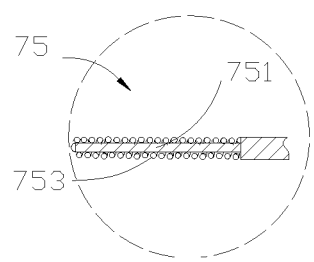
FIG. 26 is an enlarged view of the area M of FIG. 25.
Figure 27:
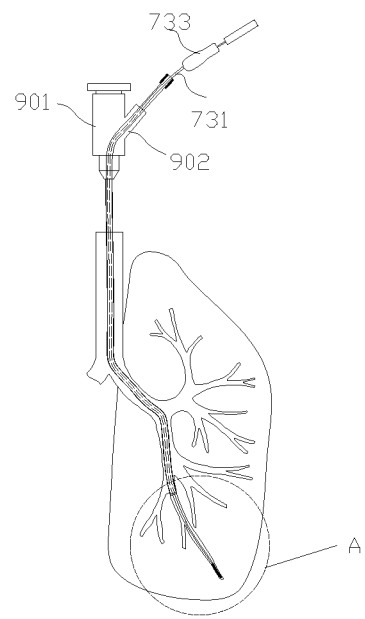
FIG. 27 is a schematic diagram showing the building of a working channel by a lung volume reduction device provided by one embodiment of the present disclosure.
Figure 28:
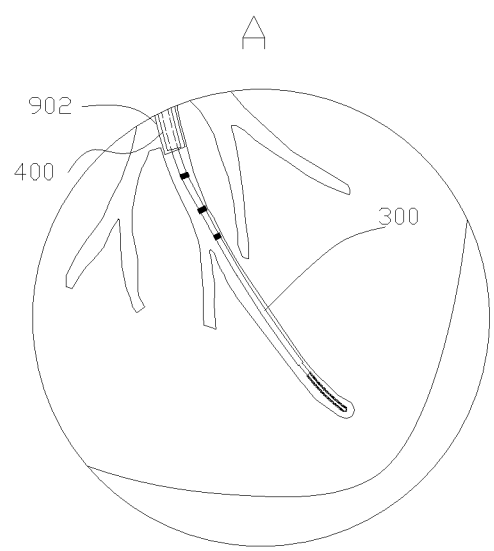
FIG. 28 is an enlarged view of the area A of FIG. 27.
Figure 29:
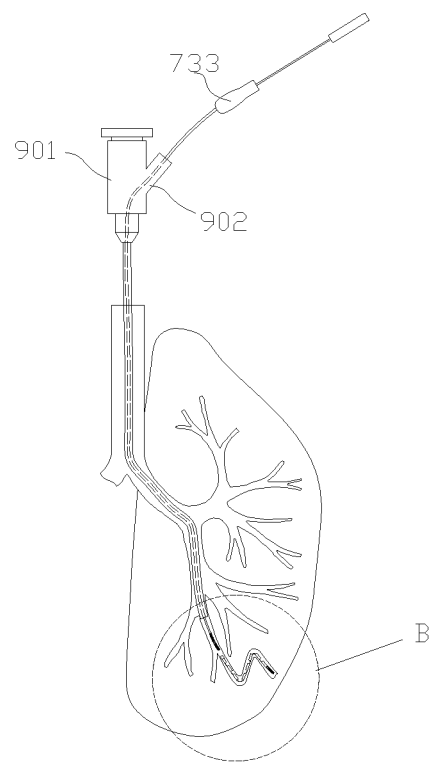
FIG. 29 is a schematic diagram after the implant is released.
Figure 30:
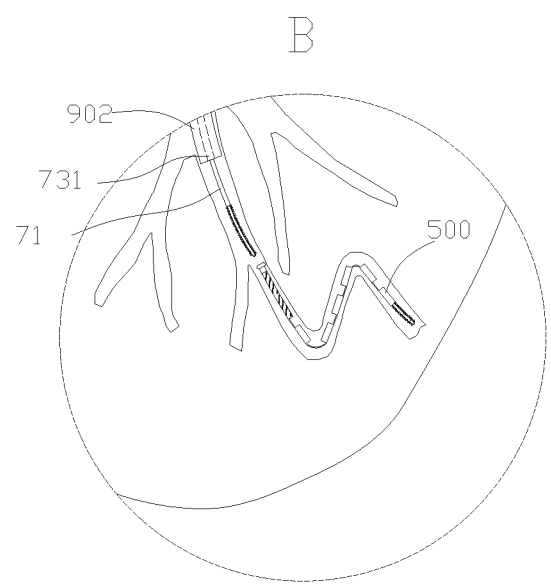
FIG. 30 is an enlarged view of the area B of FIG. 29.

Referring to FIGS. 25 and 26 together, to promote a safe and convenient operation, a flexible core wire guide head 75 coaxial with the core wire 71 and provided with a developing mark is arranged at the distal end of the core wire 71. The outer diameter of the core wire guide head 75 is consistent with that of the core wire 71. The core wire guide head 75 includes a guide column 751 and a spring 753 surrounding and fixedly arranged outside the guide column 751. The guide column 751 and the core wire 71 can be made in one piece, or the guide column 751 is fixedly connected to the distal end of the core wire 71. The spring 753 is provided with a developing mark.

The core wire guide head 75 is used for guiding the core wire 71 to enter the lumen of the elastic implant 500. The flexible core wire guide head 75 may be implemented using a soft spring, that is, the spring 753 is arranged on the guide column 751 which is made in one piece with the core wire 71 or fixedly connected to and surrounding the distal end of the core wire 71. A specific manufacturing method is as follows: the head end of the core wire 71 is thinned to prepare the guide column 751, and then one section of spring 753 having a length of 5-150 mm is fixed outside the guide column 751. The spring 753 may be fixed on the core wire 71 by the covering of a macromolecular thermal shrinkage tube or thin film, gluing, laser welding, soldering, and the like. Under the guidance of the flexible core wire guide head 75, the core wire 71 may enter the lumen of the implant 500 successfully from the proximal end of the implant 500 and may restrain the implant 500 from the shape as shown in FIG. 2 into the approximately linear shape (as shown in FIG. 23).

In the present embodiment, due to the existence of the flexible guide portion 53, the implant 500 with the core wire 71 also has an effect of exploring a pathway in the bronchus to the lesion region. To guide and monitor the operation condition of the core wire 71 entering the lung, a developing mark is required to be arranged on the core wire guide head 75. The developing mark may display the implant through a fluorescent inspection system, an ultrasonic imaging system, an MRI (Magnetic Resonance Imaging) system, a computed tomography (CT) system or other remote imaging systems. There is no limitation to specific structures. The core wire 71 is displayed and guided through these systems. In the present embodiment, the spring wound by one or more metal wires, such as tungsten metal wire or tantalum metal wire, having relatively high X-ray developing performance and a wire diameter of 0.01-0.3 mm, is used as the developing mark. In the present embodiment, the developing mark and the core wire guide head 75 are combined into one component to achieve two functions. In addition to this mode, an extra developing mark may also be arranged on the core wire guide head 75. Of course, when the surface of the implant of the present disclosure is not covered by an elastic film and the implant itself is made of a developing material such as nickel-titanium alloy, the developing mark may be omitted.

The pushing mechanism 73 includes a hollow pushing member 731 and an operation handle 733 connected with the hollow pushing member 731. The hollow pushing member 731 and the implant 500 are arranged on the core wire 71 in a surrounding manner in sequence from outside to inside, and the distal end of the hollow pushing member 731 is detachably connected with the proximal end 511 of the implant 500. In the present embodiment, the hollow pushing member 731 is a pushing steel cable, and its distal end is provided with a connection matching part 735 having an external thread matched with the internal thread of the connection member 57. During assembly, the internal thread of the connection member 57 may be threadably connected with the connection matching part 735 via the external thread of the pushing mechanism 73, and the implant 500 may be reliably fixed at the distal end of the hollow pushing member 73. After the implant 500 is pushed to a corresponding position of the bronchus, the connection member 57 of the implant 500 and the connection matching part 735 of the hollow pushing member 73 are unscrewed and separated by turning around the operation handle 733 of the hollow pushing member 73. The connection member 57 and the connection matching part 735 may also be embodied as other detachable fixed connection components, such as a magnetic connection apparatus, an elastic buckle and a noose, which are respectively arranged on the implant 500 and the hollow pushing member 103 to achieve a detachable connection.

The elastic implant 500, the core wire 71 and the hollow pushing member 731 are assembled as follows: first, the elastic implant 500 is threadably connected with the connection matching part 735 at the distal end of the hollow pushing member 731 to allow the hollow pushing member 731 to be communicated with an internal channel of the elastic implant 500; and then the core wire 71 is pushed into the elastic implant 500 along the channel of the hollow pushing member 731 to restrain the curled elastic implant 500 in the natural state into a tube in an approximately linear delivery state.

Referring to FIGS. 27 to 30, a delivery catheter 400 is pushed to the distal end of the working channel along a working channel 902 of a bronchoscope 901; a measurement guide wire 300 enters the delivery catheter 400, and extends out of the delivery catheter 400 to enter into the bronchus; the delivery catheter 400 is pushed along the measurement guide wire 300 until the distal end of the delivery catheter 400 is overlapped with the distal end of the measurement guide wire 300; while maintaining the position of the delivery catheter 400 unchanged, the measurement guide wire 300 is withdrawn until it is completely withdrawn out of the delivery catheter 400; the elastic implant 500 installed with the hollow pushing member 731 is pushed along an inner cavity of the delivery catheter 400 until it can be seen under X-ray that the distal end of the elastic implant 500 is overlapped with the distal end of the delivery catheter 400; the operation handle 733 is operated to withdraw the core wire 71 from the elastic implant; along with the withdrawal of the core wire 71, the elastic implant 500 automatically recovers its natural shape from the linear delivery state restrained by the core wire 71, and may compress and pull the emphysema region in this recovery process, and also allow relatively healthy peripheral lung tissues to better exert their respiratory physiological functions to achieve a lung volume reduction effect; and the elastic implant 500 is released by operating the operation handle 733.

Figure 31:
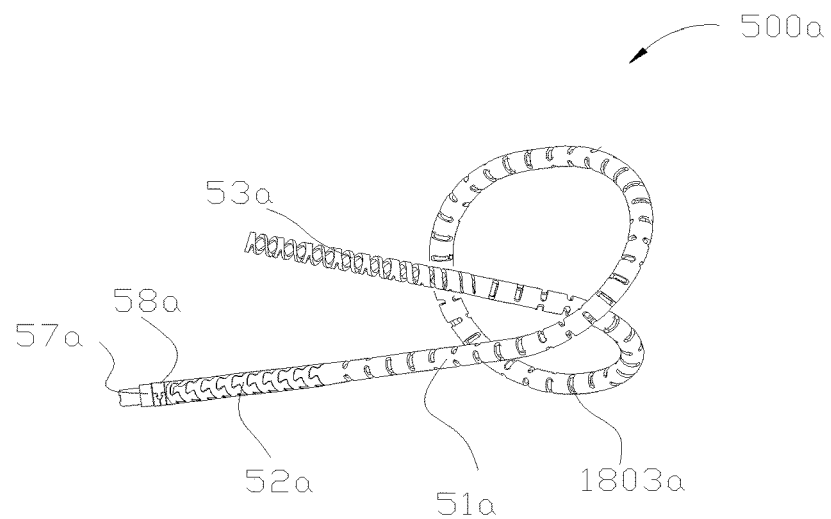
FIG. 31 is a schematic diagram of an implant provided by another embodiment of the present disclosure.

Referring to FIG. 31, an elastic implant 500a provided by another embodiment of the present disclosure includes a hollow tubular elastic deformation portion 51a, a flexible guide portion 53a connected with the distal end of the elastic deformation portion 51a, a connection portion 52a connected with the proximal end of the elastic deformation portion 51a, and a connection member 57a connected with the proximal end of the connection portion 54a. The implant 500a is at least provided with an opening in the proximal end. The elastic deformation portion 51a and the flexible guide portion 53a may be made in one piece, or fixedly connected with each other. The distal end of the flexible guide portion 53a is the distal end of the elastic implant 500a. Under the application of the same external force, the flexible guide portion 53a deforms more easily than the elastic deformation portion 51a (that is, under the application of the same external force, the anti-bending performance of the flexible guide portion 53a is lower than that of the elastic deformation portion 51a), so that the flexible guide portion 53a can experience better movement in a bronchus without injuring surrounding tissues.

Figure 32:
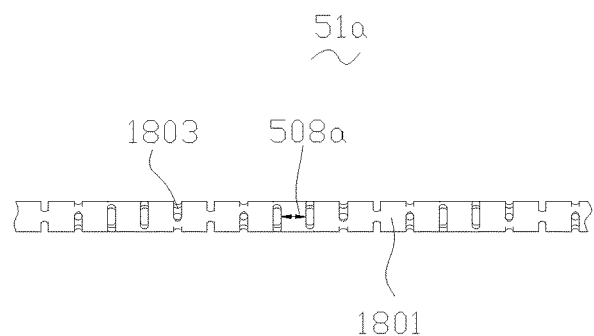
FIG. 32 is a schematic diagram of an elastic deformation portion of the implant in FIG. 31.
Figure 33:
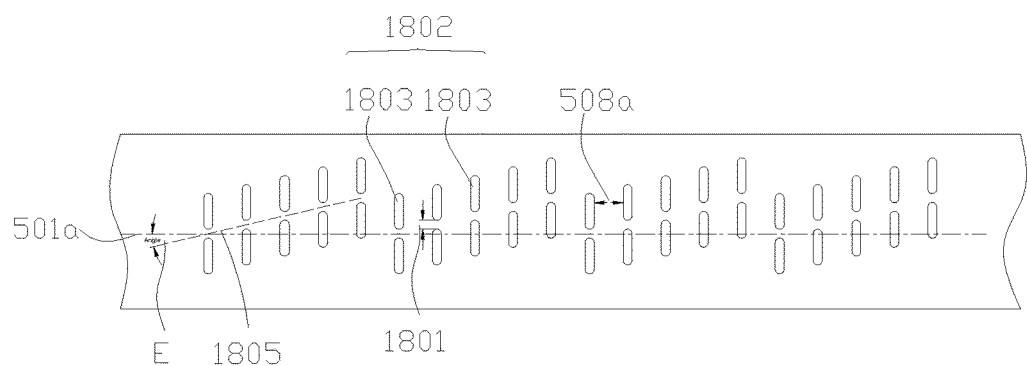
FIG. 33 is a schematic diagram of the elastic deformation portion in FIG. 32 after the elastic deformation portion is cut away along its lengthwise direction and unfolded.

Referring to FIG. 32 and FIG. 33 together, the elastic deformation portion 51a includes multiple cutting slot clusters 1802 arrayed in a spaced-apart manner along an axial direction of the elastic deformation portion 51a. Each cutting slot cluster 1802 has five side-by-side elliptical cutting slot groups 1803 arrayed in a steplike manner. In the present embodiment, each cutting slot group 1803 has two parallel cutting slots. A certain distance 1801 is provided between the two cutting slots in each cutting slot group 1803. The long axis of each cutting slot is perpendicular to the axial line of the elastic deformation portion 51a. An extension direction 1805 of the arrangement between one group and another group in each cutting slot cluster 1802 and the axial line 501a of the elastic deformation portion 51a form a certain included angle E which may be 60-90 degrees. A distance 508a of about 0.3-5 mm is provided between two adjacent cutting slot groups 1803 in each cutting slot cluster 1802. The steplike arrayed cutting slot groups 1803 are favorable for bending the elastic deformation portion 51a into a specific shape. A portion, having a length of about 0.5-5 mm, of the proximal end 511a of the elastic deformation portion 51a is cut into a threaded groove that is used as a connection member 57a. The cut nickel-titanium tube is bent into a shape as shown in FIG. 31 with a mold and then is thermally set into the elastic deformation portion 51a of the elastic implant 500a.

Figure 34:
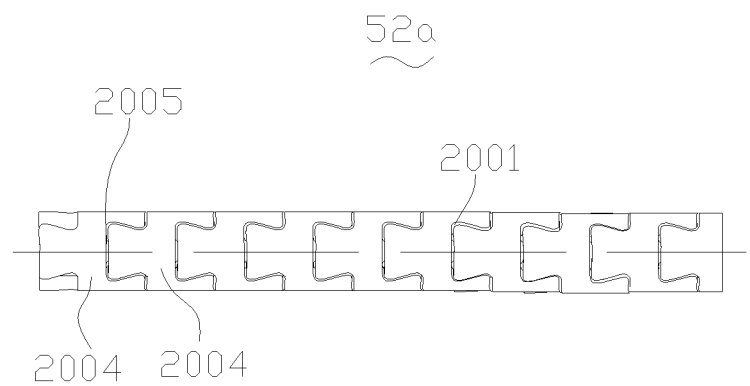
FIG. 34 is a schematic diagram of a connection portion of the implant in FIG. 31.
Figure 35:
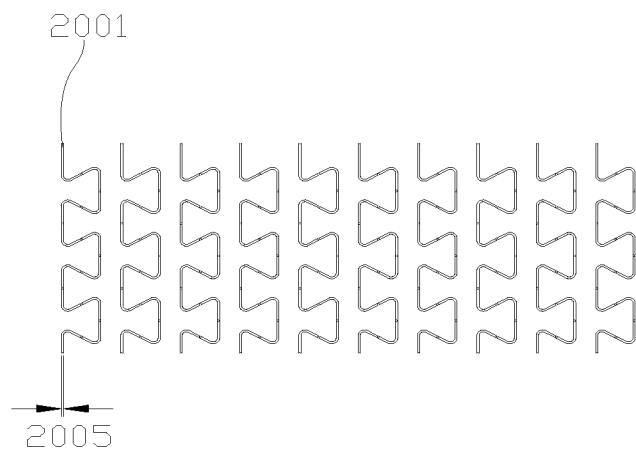
FIG. 35 is a schematic diagram of the connection portion in FIG. 34 after the connection portion is cut away along its lengthwise direction and unfolded.
Figure 36:
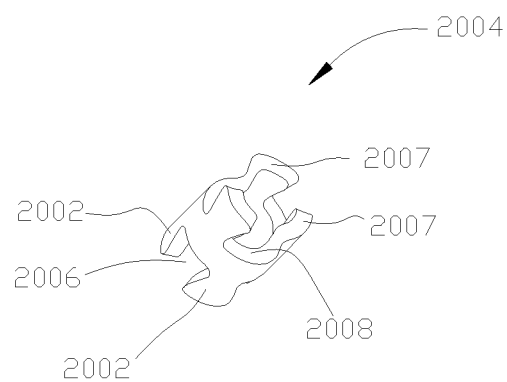
FIG. 36 is a schematic diagram of a connection sub-component of the connection portion in FIG. 34.

Under the application of the same external force, the anti-bending performance of the connection portion 52a is lower than that of the elastic deformation portion 51a so as to better reduce injury caused by the connection portion 52a to the wall of the bronchus. Referring to FIGS. 34 to 36, in the present embodiment, the connection portion 52a is a tubular body formed by connecting multiple hollow sub-components 2004 end to end, and having multiple circumferentially continuous wave-shaped cutting slots 2001. Each cutting slot 2001 has a certain width 2005. Preferably, the width of each cutting slot may be 0.01-0.3 mm. The start point and the end point of two adjacent wave-shaped cutting slots 2001 are overlapped in the circumferential direction of the connection portion 52a. Preferably, in the present embodiment, the proximal end of each sub-component 2004 includes multiple proximal end protrusions 2002 distributed in an equal spaced-apart manner along the circumferential direction of the hollow sub-component 2004. The circumferential length of each proximal end protrusion 2002 from the proximal end to the distal end is gradually decreased, so that a dovetail-shaped proximal end groove 2006 having an opening facing the proximal end is formed between two adjacent proximal end protrusions 2002. The distal end of each hollow sub-component 2004 includes multiple distal end protrusions 2007 distributed in an equal spaced-apart manner along the circumferential direction of the hollow sub-component 2004. The circumferential length of each distal end protrusion 2007 from the proximal end to the distal end is gradually increased, so that a dovetail-shaped distal end groove 2008 having an opening facing the distal end is formed between two adjacent distal end protrusions 2007. The number of the proximal end protrusions 2002 of each hollow sub-component 2004 is equal to that of the distal end protrusions 2008 of the same hollow sub-component 2004, and one distal end groove 2008 on each hollow sub-component 2004 is aligned with one proximal end protrusion 2002 on the same hollow sub-component 2004. In this way, in two hollow sub-components 2004, the multiple dovetail-shaped proximal end protrusions 2002 on one hollow sub-component 2004 mesh with the multiple distal end grooves 2008 of the other hollow sub-component 2004, so that the two mutually separated hollow sub-components 2004 form an interlocked structure, and the multiple hollow sub-components 2004 are spliced and combined into the connection portion 52a. As all the mutually separated hollow sub-components 2004 are connected through meshing structures of the dovetail-shaped protrusions and the dovetail grooves, the connection portion 52a of this structure has extremely high flexibility and extremely high connection strength and may transmit a torsion to the elastic deformation portion 51a in a ratio of 1:1 during twisting of the connection member 57. On the basis of the prior art, the sub-components 2004 may also be made using by other techniques such as machining, casting and powder metallurgy. It can be understood that the connection portion 52a is extremely flexible and extremely low in anti-bending performance, so it is very easy to make the anti-bending performance of the connection portion 52a lower than that of the elastic deformation portion 51a by adjusting the anti-bending performance of the elastic deformation portion 51a. It can be understood that the multiple proximal end protrusions 2002 also may be distributed at the proximal ends of the sub-components 2004 in non-equal spacings as long as the multiple sub-components 2004 may be spliced.

Figure 37:
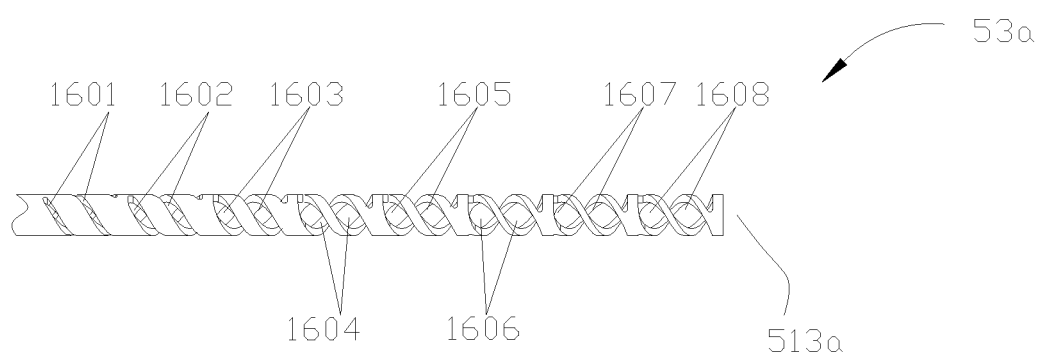
FIG. 37 is a schematic diagram of a flexible guide portion of the implant in FIG. 31.
Figure 38:
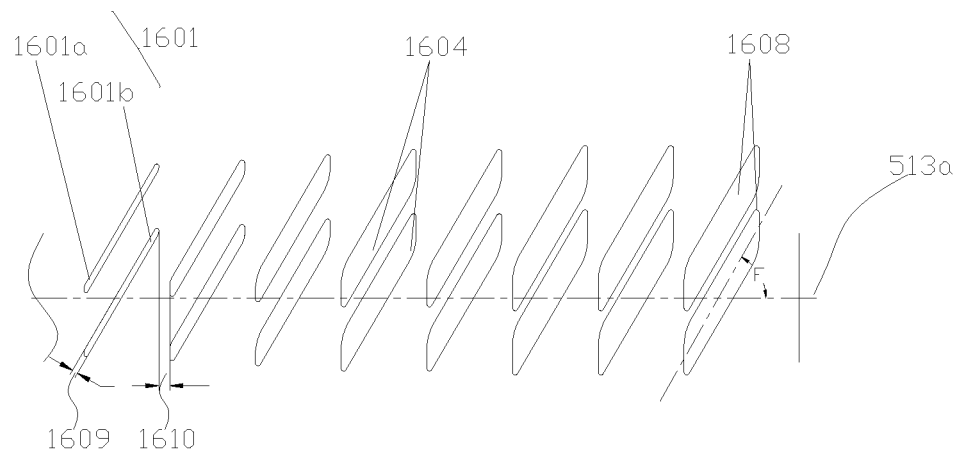
FIG. 38 is a partial schematic diagram of the flexible guide portion in FIG. 32 after the flexible guide portion is cut away along its lengthwise direction and unfolded.

Under the application of the same external force, the anti-bending performance of the flexible guide portion 53a is lower than that of the elastic deformation portion 51a so as to better guide the elastic deformation portion 51a to move in the bronchus and to reduce the chance of injury to the wall of the bronchus. Under the application of the same external force, the anti-bending performance of the flexible guide portion 53a from the distal end to the proximal end is gradually improved. Referring to FIGS. 37 and 38 together, in the present embodiment, the flexible guide portion 53a is a tubular body cut from a nickel-titanium tube through laser and having cutting slots, and under the application of the same external force, the anti-bending performance of the flexible guide portion 53a from the distal end to the proximal end is gradually improved (that is, under the application of the same external force, the deformation performance of the flexible guide portion 53a from the distal end to the proximal end is gradually lowered, namely the flexible guide portion 53a becomes progressively harder from the distal end to the proximal end) so as to better guide the elastic implant 500. It can be understood that as the flexible guide portion 53a is the tubular body having the multiple cutting slots, the anti-bending performance of the flexible guide portion 53a may vary with changes in the distances between adjacent cutting slots. Those skilled in the art can set the distances between adjacent cutting slots according to clinical requirements to make the anti-bending performance of the flexible guide portion 53a lower than that of the elastic deformation portion 51a.

The flexible guide portion 53a includes multiple slender cutting slot groups 1601-1608. Each cutting slot group (such as 1601) is composed of two or more parallel cutting slots 1601a and 1601b, and each parallel cutting slot has a certain width 1609. The extension direction of these cutting slot groups 1601-1608 and the axial line 513a of the flexible guide portion 53a form a certain angle F. A gap 1610 is provided between two adjacent cutting slot groups. By adjusting the number and the width 1609 of the cutting slots in each cutting slot group, the size of the angle F and the size of each gap 1610, the anti-bending performance of the flexible guide portion 53a may be adjusted. Preferably, there may be 2-6 parallel cutting slots 1601, the width 1609 may be 0.05-1 mm, the angle F is preferably 5-85 degrees, and the gap 1610 is preferably 0.1-1.0 mm. The parallel cutting slot groups (1601-1608) having different widths 1609 are combined into the same nickel-titanium tube to fulfill the objective of gradually improving the anti-bending performance of the flexible guide portion 53a from the distal end to the proximal end under the application of the same external force. The flexible guide portion 53a having the gradually changing anti-bending performance may be more effective in guiding the elastic implant 500a.

The connection between the flexible guide portion 53a and the elastic deformation portion 51a may be implemented by techniques such as covering a macromolecular thermal shrinkage tube or thin film, gluing, laser welding, soldering, and the like. On the basis of the prior art, integrated cutting is preferred, and the flexible guide portion 53a and the elastic deformation portion 51a which have different textural features are cut from different areas on the same tube. To achieve the gradually changing anti-bending performance of the flexible guide portion 53a, one feasible mode is to maintain the angle F in two adjacent cutting slot groups unchanged, and to gradually decrease the width 1609 of each cutting slot from the distal end to the proximal end, and another feasible mode is to maintain the width 1609 of each cutting slot in two adjacent cutting slot groups unchanged, and to gradually increase the angle F from the distal end to the proximal end. It can be understood that simultaneously changing the angle F and the width 1609 of each cutting slot in two adjacent cutting slot groups may also achieve the effect of gradually improving the anti-bending performance of the flexible guide portion 53a from the distal end to the proximal end.

Figure 39:
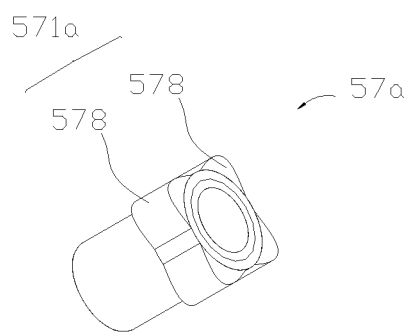
FIG. 39 is a schematic diagram of a connection member of the implant in FIG. 31.
Figure 40:
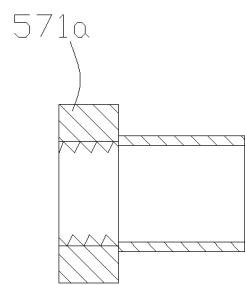
FIG. 40 is a sectional view of the connection member in FIG. 39.
Figure 41:
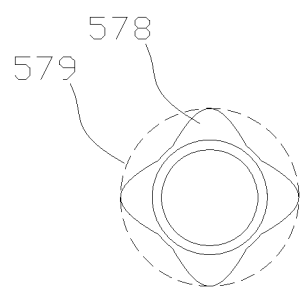
FIG. 41 is a top view of the proximal end side of the connection member in FIG. 39.

Referring to FIG. 39 and FIG. 40, the connection member 57a is approximately the same as the connection member 57, but a difference lies in the fact that the boss 571a of the connection member 57a has multiple small protrusions 578 distributed in an equal spacing along its circumferential direction and connected with one another. Referring to FIG. 41, the multiple small protrusions 578 taken together define a virtual circumference 579 (namely a circumscribed circle of the multiple small protrusions 578 is 579). The diameter of the circumference 579 is the outer diameter of the boss 571a. Due to the existence of the small protrusions 578, a fastening position is provided for biopsy forceps, so that the biopsy forceps can clamp a connection apparatus more effectively to withdraw the elastic implant 500a. The connection between the connection member 57a and the connection portion 52a may be implemented by techniques such as covering of a macromolecular thermal shrinkage tube or thin film, gluing, laser welding, soldering and the like.

Figure 42:
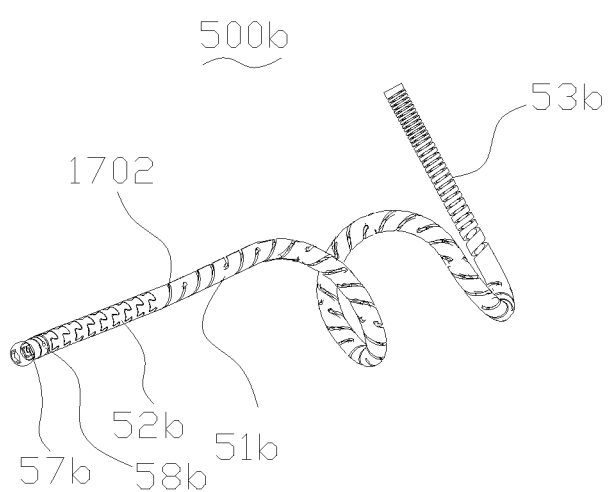
FIG. 42 is a schematic diagram of an elastic implant provided by another embodiment.
Figure 43:
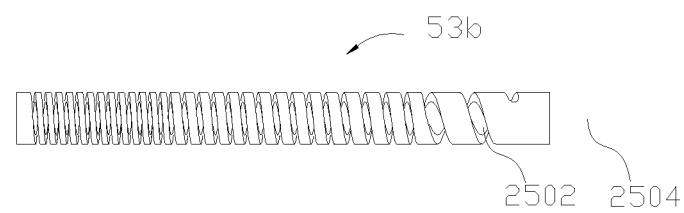
FIG. 43 is a schematic diagram of a flexible guide portion of the implant in FIG. 42.

Referring to FIG. 42, an elastic implant 500b provided by another embodiment of the present disclosure includes a hollow tubular elastic deformation portion 51b, a flexible guide portion 53b connected with the distal end of the elastic deformation portion 51b, a connection portion 52b connected with the proximal end of the elastic deformation portion 51b, and a connection member 57b connected with the proximal end of the connection portion 54b. The implant 500b is at least provided with an opening in the proximal end. The elastic deformation portion 51b and the flexible guide portion 53b may be made in one piece or fixedly connected. The distal end of the flexible guide portion 53b is the distal end of the elastic implant 500b. Under the application of the same external force, the flexible guide portion 53b deforms more easily than the elastic deformation portion 51b, so that the flexible guide portion 53b can move more effectively in a bronchus without injuring surrounding tissues.

The arrangement mode of the cutting slots of the elastic deformation portion 51b is approximately the same as that of the cutting slots of the connection portion 52 in the one Embodiment above, and no more details will be described here.

Figure 44:
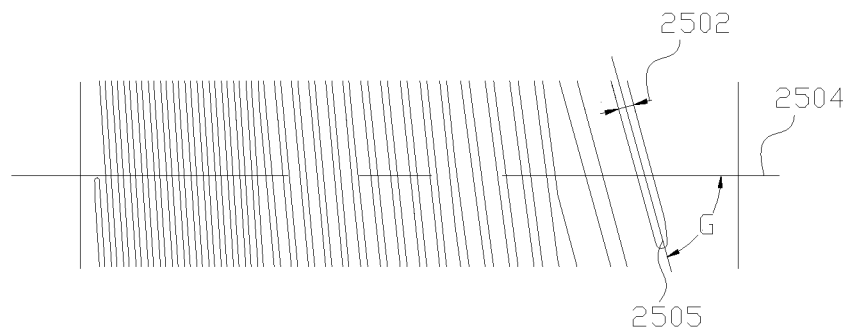
FIG. 44 is a schematic diagram of the flexible guide portion in FIG. 43 after the flexible guide portion is cut away along its lengthwise direction and unfolded.
Figure 45:
FIG. 45 is a schematic diagram of an integrated structure of the elastic deformation portion, the flexible guide portion and the connection portion.

Referring to FIGS. 44 and 45 together, the flexible guide portion 53b is a tubular body cut from a nickel-titanium tube by laser and having continuously spiral cutting slots, and under the application of the same external force, the anti-bending performance of the flexible guide portion 53b from the distal end to the proximal end is gradually improved (that is, under the application of the same external force, the deformation performance of the flexible guide portion 53a from the distal end to the proximal end is gradually lowered) so as to better guide the elastic implant 500b. It can be understood that as the flexible guide portion 53b is the tubular body having the continuously spiral cutting slots, the anti-bending performance of the flexible guide portion 53b may vary with changes in the distances between adjacent cutting slots. Those skilled in the art can set the distances between adjacent cutting slots according to clinical requirements to make the anti-bending performance of the flexible guide portion 53b lower than that of the elastic deformation portion 51b.

The flexible guide portion 53b includes the continuously spiral cutting slots 2502. In a planar view showing the flexible guide portion 53b cut away along its axial direction, the distance between two adjacent cutting slots 2502 is also gradually increased from the distal end to the proximal end of the flexible guide portion 53b to gradually improve the anti-bending performance of the flexible guide portion 53b from the distal end to the proximal end.

It can be understood that, on the planar view showing the flexible guide portion 53b cut away along its axial direction, from the distal end to the proximal end of the flexible guide portion 53b, when an included angle G between the extension direction 2505 of the cutting slots 2502 of the flexible guide portion 53b and the axial direction 2504 of the flexible guide portion 53b is unchanged and the width of each cutting slot of the flexible guide portion 53b along the axial direction 2504 of the flexible guide portion 53b is gradually decreased, the distance between two adjacent cutting slots 2502 is gradually increased as well so as to gradually improve the anti-bending performance of the flexible guide portion 53b from the distal end to the proximal end.

It can be understood that, on the planar view showing the flexible guide portion 53b cut away along its axial direction, from the distal end to the proximal end of the flexible guide portion 53b, when the width of each cutting slot of the flexible guide portion 53b along the axial direction 2504 of the flexible guide portion 53b is unchanged and the included acute angle between the extending direction 2505 of the cutting slots of the flexible guide portion 53b and the axial direction 2504 of the flexible guide portion 53b is gradually increased, the distance between two adjacent cutting slots 2502 is gradually increased as well so as to gradually improve the anti-bending performance of the flexible guide portion 53b from the distal end to the proximal end.

The structure of the connection portion 52b is approximately the same as that of the connection portion 52a, and no more details will be described here.

Preferably, an integrated molding mode is adopted. The features of the elastic deformation portion 51b, the flexible guide portion 53b and the connection portion 52b which are cut from the same nickel-titanium tube by laser are as shown in FIG. 45, and the problems of low connection strength and the like caused by the connection mode may be avoided.

Figure 46:
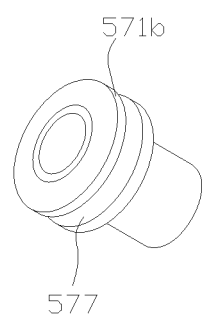
FIG. 46 is a schematic diagram of a connection member of the elastic implant in FIG. 42.
Figure 47:
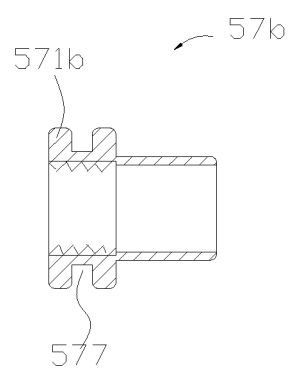
FIG. 47 is a sectional view of the connection member in FIG. 46.

Referring to FIG. 46 and FIG. 47 together, the connection member 57b is approximately the same as the connection member 57, but a difference lies in the fact that part of the side surface of a boss 571b of the connection member 57b is sunken into the inside of the boss 571b to form an annular groove 577 surrounding the longitudinal center line of the boss 571b.

The embodiments of the present disclosure are described above in combination of the accompanying drawings, but the present disclosure is not limited to the above-mentioned specific implementation modes. The above-mentioned specific implementation modes are merely schematic, but not restrictive. Those of ordinary skills in the art can make many forms under the enlightenment of the present disclosure without departing from the purpose of the present disclosure and the scope protected by claims, and these forms shall all fall within the protection of the present disclosure.

The invention claimed is:

1. An implant comprising:
   an elastic deformation portion having a proximal end;
   a connection portion connected with the proximal end of the elastic deformation portion, the connection portion having a proximal end and a distal end which is attached to and extending from the proximal end of the elastic deformation portion;
   an elastic outer layer covering the elastic deformation portion, the elastic outer layer having a proximal end;
   a tightening ring provided on the proximal end of the connection portion and forming an outer jacket covering the proximal end of the connection portion; and
   wherein the tightening ring also covers the proximal end of the elastic outer layer.

2. The implant of claim 1, wherein the implant is a lung volume reduction implant.

3. An implant comprising:
   an elastic deformation portion having a proximal end;
   a connection portion connected with the proximal end of the elastic deformation portion, the connection portion having a proximal end;
   an elastic outer layer covering the elastic deformation portion, the elastic outer layer having a proximal end;
   a tightening ring provided on the proximal end of the connection portion and forming an outer jacket covering the proximal end of the connection portion;
   wherein the tightening ring also covers the proximal end of the elastic outer layer; and
   wherein the tightening ring has a first end which is provided with a connection plug, and a second end opposite to the first end which is provided with an insertion slot that is inserted into the connection plug.

4. The implant of claim 3, wherein the tightening ring has a thin slot that communicates with the insertion slot, and wherein the thin slot is located on one side of the insertion slot away from the connection plug.

5. The implant of claim 4, wherein the tightening ring is further provided with a through hole that communicates with the insertion slot, and the through hole and the insertion slot are respectively located at two opposite ends of the thin slot.

6. The implant of claim 5, wherein the thin slot of the tightening ring has a center line and an extension line, and wherein the center of the through hole is located on the extension line.

7. The implant of claim 5, wherein the through hole has a diameter and the tightening ring has a width, and wherein the ratio of the diameter of the through hole to the width of the tightening ring ranges between 0.2:1 and 0.6:1.

8. The implant of claim 3, wherein the connection plug has a T-shaped configuration, and the connection plug comprises a head portion and a neck portion connected with the head portion, and a connection part which connects the head portion with the neck portion, wherein the neck portion and the connection part both have an axial width, and the axial width of the neck portion that is less than the axial width of the connection part.

9. The implant of claim 8, wherein the head portion has an axial width that is gradually increased along a direction close to the neck portion.

10. The implant of claim 9, wherein the head portion has an inner edge, with an included angle defined between the inner edge of the head portion of the connection plug along the axial line of the tightening ring, and the included angle ranges from 45 to 85 degrees.

11. An implant comprising:
   an elastic deformation portion having a proximal end;
   a connection portion connected with the proximal end of the elastic deformation portion, the connection portion having a proximal end;
   an elastic outer layer covering the elastic deformation portion, the elastic outer layer having a proximal end;
   a tightening ring provided on the proximal end of the connection portion and forming an outer jacket covering the proximal end of the connection portion;
   wherein the tightening ring also covers the proximal end of the elastic outer layer;
   the implant further including a flexible guide portion, and wherein:
   the elastic deformation portion has a shape memory characteristic, and the flexible guide portion deforms more easily than the elastic deformation portion;
   the proximal end of the connection portion is further provided with a boss;
   and
   the boss has an outer diameter that is greater than that of the proximal end of the connection portion when in a delivery state.

12. The implant of claim 11, wherein the flexible guide portion deforms more easily from its proximal end to its distal end.

13. The implant of claim 11, wherein the connection portion deforms more easily than the elastic deformation portion.

14. The implant of claim 13, wherein the connection portion has a lumen, and the connection portion is provided with a plurality of cutting slots in a spaced-apart manner along a lengthwise direction of the connection portion, and all the cutting slots of the connection portion communicate with the lumen of the connection portion.

15. The implant of claim 13, wherein:
   the connection portion comprises a plurality of hollow sub-components connected end to end, wherein each hollow sub-component has a distal end and a proximal end;
   the proximal end of each hollow sub-component comprises a plurality of proximal end protrusions distributed along a circumferential direction of the hollow sub-component;
   the circumferential length of each proximal end protrusion from the proximal end of the hollow sub-component to the distal end of the hollow sub-component is gradually decreased, and a proximal end groove is formed between two adjacent proximal end protrusions;
   the distal end of each hollow sub-component comprises a plurality of distal end protrusions distributed along the circumferential direction of the hollow sub-component, with each distal end protrusion having a circumferential length; and
   the circumferential length of each distal end protrusion from the proximal end of the hollow sub-component to the distal end of the hollow sub-component is gradually increased, and a distal end groove is formed between two adjacent distal end protrusions.

16. The implant of claim 11, wherein the boss has a proximal end, a distal-end face, and a longitudinal center line, and wherein part of the distal-end face of the boss is sunken towards the proximal end of the boss to form an annular groove surrounding the longitudinal center line of the boss.

17. The implant of claim 11, wherein the boss has a side surface, and a longitudinal center line, and wherein part of the side surface of the boss is sunken into the boss to form an annular groove surrounding the longitudinal center line of the boss.

18. The implant of claim 11, wherein the boss has a circumferential direction, and comprises a plurality of small protrusions distributed in a spaced-apart manner along the circumferential direction of the boss.

* * * * *